United States Patent
Ramsey et al.

(10) Patent No.: US 7,766,897 B2
(45) Date of Patent: Aug. 3, 2010

(54) PROTECTIVE PRIMING CAP FOR SELF-SEALING MALE LUER VALVE

(75) Inventors: Michael D. Ramsey, Raleigh, NC (US); Kenneth W. Whitley, Raleigh, NC (US); John C. Phillips, New Hill, NC (US)

(73) Assignee: Carefusion 303, Inc., San Diego, CA (US)

( * ) Notice: Subject to any disclaimer, the term of this patent is extended or adjusted under 35 U.S.C. 154(b) by 413 days.

(21) Appl. No.: 11/324,410

(22) Filed: Jan. 2, 2006

(65) Prior Publication Data

US 2007/0156118 A1    Jul. 5, 2007

(51) Int. Cl.
*A61M 39/10* (2006.01)
*A61M 39/00* (2006.01)
*A61M 25/16* (2006.01)
*A61M 25/18* (2006.01)

(52) U.S. Cl. ................................. 604/533; 604/537
(58) Field of Classification Search ......... 604/533–539, 604/167, 168, 256, 122; 137/614.05, 614.06
See application file for complete search history.

(56) References Cited

U.S. PATENT DOCUMENTS

| | | | | |
|---|---|---|---|---|
| 4,738,668 A | * | 4/1988 | Bellotti et al. ............... | 604/533 |
| 4,758,225 A | * | 7/1988 | Cox et al. .................... | 604/126 |
| 4,935,010 A | | 6/1990 | Cox et al. | |
| 5,006,114 A | * | 4/1991 | Rogers et al. ................ | 604/245 |
| 5,032,116 A | * | 7/1991 | Peterson et al. ......... | 604/168.01 |
| 5,122,123 A | | 6/1992 | Vaillancourt | |
| 5,127,904 A | | 7/1992 | Loo et al. | |
| 5,242,411 A | * | 9/1993 | Yamamoto et al. ..... | 604/167.04 |
| 5,356,376 A | | 10/1994 | Milijasevic et al. | |
| 5,445,630 A | | 8/1995 | Richmond | |
| 5,735,826 A | | 4/1998 | Richmond | |
| 5,814,015 A | | 9/1998 | Gargano et al. | |
| 5,820,596 A | * | 10/1998 | Rosen et al. ................. | 604/108 |
| 6,152,913 A | | 11/2000 | Feith et al. | |
| 6,344,033 B1 | | 2/2002 | Jepson et al. | |
| 6,575,960 B2 | | 6/2003 | Becker et al. | |

(Continued)

OTHER PUBLICATIONS

PCT International Search Report for International Application No. PCT/US06/49166 mailed Sep. 11, 2007.

*Primary Examiner*—Kevin C Sirmons
*Assistant Examiner*—Michael J Anderson
(74) *Attorney, Agent, or Firm*—McDermott Will & Emery LLP (57) ABSTRACT

A cap for use in priming a medical connector that has a distal end at which is disposed a distal connection tip with an aperture through which fluid may flow, and the connector having an internal valve. The cap has a reservoir device with an internal volume and a first opening at a proximal end that is connected with the aperture of the connection tip. The reservoir has a second opening at which is disposed an hydrophobic filter for allowing gases to vent to the atmosphere while retaining liquid in the reservoir device. Over the reservoir device is mounted a slidable housing device used to activate the internal valve of the connector to a flow configuration at which fluid flows from the connector into the reservoir device. The user monitors the reservoir device and when gas has been vented so that only liquid remains, the user slides the housing device.

17 Claims, 4 Drawing Sheets

U.S. PATENT DOCUMENTS

| | | | |
|---|---|---|---|
| 7,100,890 B2 * | 9/2006 | Cote et al. | 251/149.1 |
| 7,160,267 B2 * | 1/2007 | Brown | 604/122 |
| 7,226,432 B2 * | 6/2007 | Brown | 604/122 |
| 2003/0220599 A1 | 11/2003 | Lundtveit et al. | |
| 2004/0124389 A1 | 7/2004 | Phillips | |
| 2007/0017583 A1 * | 1/2007 | Fangrow | 137/614.06 |
| 2007/0088324 A1 * | 4/2007 | Fangrow | 604/533 |
| 2007/0088325 A1 * | 4/2007 | Fangrow | 604/533 |
| 2007/0156118 A1 * | 7/2007 | Ramsey et al. | 604/533 |

* cited by examiner

PROTECTIVE PRIMING CAP FOR SELF-SEALING MALE LUER VALVE

BACKGROUND OF THE INVENTION

The present invention generally relates to a system and method for priming medical administration sets for conducting fluids to patients, and more particularly, to a system and method used for protecting and priming medical connectors.

Many self-sealing connectors presently known and used in the medical art are designed to be connected to a patient's intravenous ("IV") or gas sampling line, drug or solution source, or other medical device such that the connector's seal operates to trap all fluid on the side of the connector toward the patient in the case of an IV line, on the side of other device such as a fluid bag in the case of a fluid source. Such seals often take the form of a valve located internally to the connector. In the case of many connectors used today, the connection tip has a Luer shape in accordance with ISO 594 whether the connection tip is male or female. In some cases, the Luer connector has an unsealed male Luer connection tip on one end that remains connected to the patient's IV line, fluid source, or other device and a self-sealing female Luer connector on the opposite free end of the connector through which a syringe or other such device may be engaged. In the case of other connectors, the connector does not have a separate male connector end but that end is instead a permanent part of the line or source.

In use, a syringe or other device having a male Luer connector is connected to the female end of the self-sealing Luer connector to push or pull fluids through the female connector, as when medications are dispensed within a patient's IV line. The syringe or other device is configured with a male Luer connector so as to engage the self-sealing female connector and cause the male Luer connector's central boss to contact the female Luer connector's seal, opening the valve and creating a fluid path through the female connector. After the necessary fluids have been dispensed or withdrawn, the syringe is removed and the internal valve of the female connector closes to reseal the female connector and trap all bodily fluids, including any just-dispensed medications, on the patient side of the connector.

Therefore, the bodily fluids are sealed off within the self-sealing female Luer connector toward the patient and away from the clinician preventing any escape of the fluids and protecting both the patient and the clinician from possible dangerous contamination from the IV administration set. Until recently, the free end of the syringe and any residual fluids remaining therein are unsealed and exposed. Rather than the self-sealing, needle-free connectors known in the art remaining attached to the syringe to trap any and all residual fluids within the syringe, they remain on the destination or source connector to trap all residual fluids there instead. However, self-sealing male connectors have been developed. Such self-sealing male connectors have internal valves and have been recognized as having many advantages including the advantage of trapping residual fluid in the fluid line or device, such as a syringe, to which they are attached when the male sealed connector is disconnected from a female connector. This is a distinct advantage when toxic medical fluids are involved.

As is well known to those skilled in the art, the use of infusion devices, including IV medical fluid administration sets and medical fluid connectors, male or female, requires that the supply tube and connectors be purged of air or "primed" prior to initiation of fluid flow into the patient. While patients can tolerate receiving a certain level of air from an IV medical fluid line, too high of a level can result in an air embolism with an adverse effect on the patient. In most cases, supply tubes and connectors initially contain a dead space volume of air. A priming procedure for purging this volume of air must typically be performed prior to connection of the supply tube and connectors to the patient.

Currently, most IV lines are primed by holding the distal fitting over a waste-bin in one hand while allowing the line to flow. The flow rate while priming is regulated with a roller clamp attached to the IV line that the user holds in his/her other hand. The user must watch the line and close the roller clamp as fluid reaches the tip of the distal fitting. Frequently, some fluid drips into the waste-bin before the clamp can be closed. This is not desirable if the fluid that drips out is either expensive or toxic. For example, in the area of nuclear medicine where radioactive isotopes are administered to patients, it is critical that exposure to the isotopes be minimized for the safety of both the care giver and the patient. Yet a further example is in the oncology area where certain drugs have great beneficial effect when confined to the circulatory system of a patient, yet are harmful to the skin or other tissue of a patient. Such drugs must be carefully controlled so that they do not reach tissues that may be harmed. Transferring such drugs from one container to another or to the patient's fluid line can be hazardous if seals are not present. The same or similar procedure would be used with other medical devices with which medical fluid is to be infused into the patient.

Initially in the case of an IV administration set, the proximal end of the supply tube is attached to the supply reservoir. The distal end of the supply tube is initially closed off using a tube clamp. For priming the supply tube, the tube clamp is adjusted, opening the supply tube and initiating liquid flow from the supply reservoir through the supply tube. This forces the dead volume of air initially contained in the supply tube out the distal end of the supply tube. When liquid reaches the distal end of the supply tube, the air in the supply tube has been purged. The supply tube is then closed off by adjusting the tube clamp and the distal end of the supply tube is attached to the patient interface device. It is at this point that typically some fluid drips out of the line before it can be closed; i.e., the undesirable situation discussed above.

In the case of sealed male Luer connectors, i.e., male connectors with internal valves, some such connectors draw fluid back into the connector upon de-activation to the non-flow configuration. This feature has been designed into such connectors for the purpose of removing any stray medical fluid from the tip of the connector during the time it is being disconnected from a female connector so that a clinician will not inadvertently come into contact with such fluid. This is a particular advantage when toxic fluids are to be administered to the patient. While this feature provides a recognized advantage during the time the connector is in use, it must be also considered during the priming process. Those skilled in the art have recognized the need for a priming system and method for such connectors.

As another consideration, patients requiring therapy have often been placed in a position where their normal defenses against microorganisms are compromised. As a result, the patients may develop nosocomial infections while being treated for another disease during therapy. As has been recognized, a possible cause of nosocomial infections can be the tubing lines and devices of medical administration sets, especially in the area of IV therapy. This is one reason why most IV administration sets (IV tubing with connectors) are carefully cleaned before use and are discarded every seventy-two hours. Protective measures, such as a protective cap mounted to the Luer tip, taken before the use of connectors are widely appreciated as having a preventive effect on infections for patients. Additionally, Luer fittings are susceptible to being damaged through rough handling and protective caps would not only lower the risk of infection to the patient, but would also lessen the risk of damage to a male Luer connection tip itself.

Hence, those skilled in the art have recognized a need for a protective cap for a self-sealing male connector to lessen the risks of damage to the connector and the risk of infection to patients. Further, those skilled in the art have recognized the need for a system and method for priming self-sealing male Luer connectors so that no liquid is wasted or exposed to clinicians. The present invention fulfills these needs and others.

SUMMARY OF THE INVENTION

Briefly and in general terms, the present invention is directed to a system and a method for protecting the connection tip of a male connector and for providing priming of the connector in which air is vented to the atmosphere while liquid is kept within a reservoir and is returned to the connector when the priming operation is complete. In a more detailed aspect, there is provided a cap for a medical connector, the connector having a distal end at which is disposed a distal connection tip, the connection tip having an aperture through which fluid may flow, and the connector having an internal valve, the cap comprising a reservoir device having an internal volume, a first opening at a proximal end, and a second opening at which is disposed an hydrophobic filter, wherein the proximal end of the reservoir device is shaped for engaging the connection tip of the connector so that the first opening of the reservoir device may be put into fluid communication with the aperture of the connector, the reservoir device being removable from the connector, and an outer housing device mounted over the reservoir device and movable in relation thereto, the outer housing device covering the distal connection tip of the connector whereby it provides protection to the distal connection tip, the housing device including an engagement portion disposed to engage the internal valve of the connector wherein the outer housing device is movable to a first position at which it covers the distal connection tip of the connector but at which the engagement portion does not open the internal valve device of the connector and is movable to a second position at which the outer housing device covers the distal end of the connector and the engagement portion opens the internal valve of the connector so that fluid flow may occur between the reservoir device and the connector, the outer housing device being removable from the connector.

In a more detailed aspect, the reservoir device is formed of a transparent material so that a level of liquid within the reservoir device may be seen. In another aspect, the outer housing device includes a window through which the level of liquid in the reservoir device can be seen through the outer housing device, and in further detail, the outer housing device is formed at least partially of a transparent material so that the level of liquid in the reservoir device can be seen through the outer housing device.

Turning to yet further detailed aspects, the distal connection tip comprises a male Luer tip and the reservoir device has a shape complementary to the male Luer tip allowing the reservoir tip to engage the male Luer tip for communication of fluid between the two. The outer housing device is slidable along the reservoir device between the first and second positions.

In yet further more detailed aspect, the reservoir device is attached to the connector and in another aspect, the reservoir device is threaded to the connector to establish attachment. A tactile structure configured to provide a tactile feedback to a clinician rotating the reservoir device in relation to the connector when the reservoir device has been threadably rotated sufficiently to establish a seal with the connector. The reservoir device comprises an inner surface having irregularities configured to increase the surface tension of liquid within the reservoir whereby escape of the liquid from the reservoir device is inhibited. The cap further comprises a lock device configured to retain the outer housing device in a position at which an internal valve of the connector is activated to a flow position.

In another detailed aspect in accordance with the invention, there is provided a cap for use with a medical connector that draws back a quantity of fluid when the internal valve moves to a non-flow configuration, wherein the internal volume of the reservoir device of the cap is approximately equal to the quantity of fluid drawn back into the connector when the internal connector valve moves to the non-flow configuration. Further, the reservoir device is assembled within the outer housing device to form the cap and is removed from the connector as one piece.

In accordance with method aspects of the invention, there is provided a method for priming a medical connector, the connector having a distal end at which is disposed a distal connection tip, the connection tip having an aperture through which fluid may flow, and the connector having an internal valve, the method comprising mounting a reservoir device having an internal volume, a first opening at a proximal end, and a second opening at which is disposed an hydrophobic filter at the connection tip of the connector with the first opening in fluid communication with the aperture of the connection tip, activating the internal valve of the connector to a flow configuration, allowing fluid to flow through the connector and into the reservoir, allowing any gas in the reservoir to escape through the hydrophobic filter, de-activating the internal valve of the connector to a non-flow configuration, and removing the reservoir device from the connection tip.

These and other aspects, features, and advantages of the present invention will become apparent from the following detailed description of the preferred embodiments which, taken in conjunction with the accompanying drawings, illustrate by way of example the principles of the invention.

DETAILED DESCRIPTION OF THE INVENTION

Figure 1:
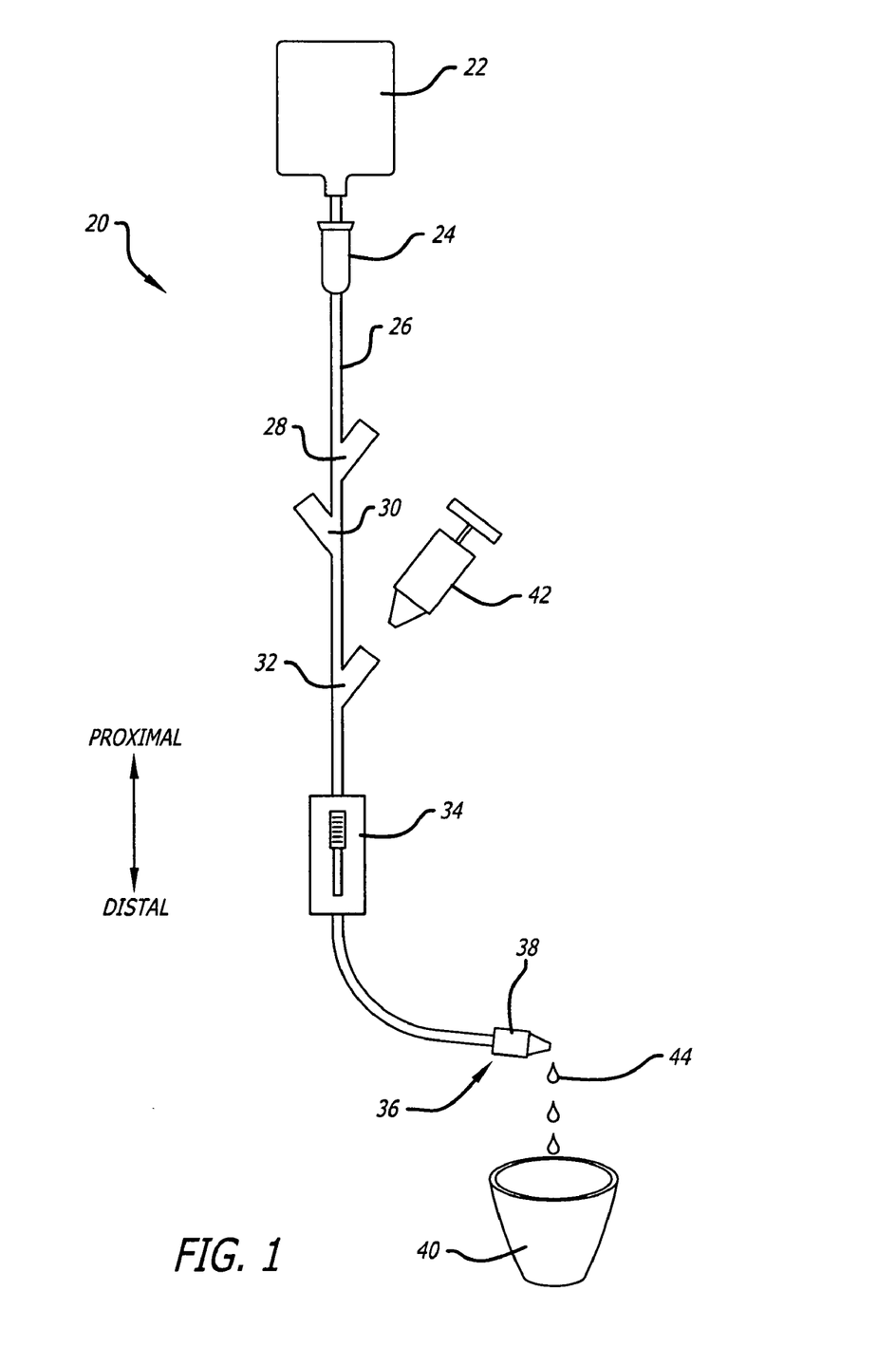
FIG. 1 is an overview, block-type diagram showing an IV medical fluid administration system having a reservoir of medical fluid to be administered, a tubing through which the fluid is to be conducted, multiple Y-sites formed into the tubing, at least one of which has a self-sealing female Luer connector providing a port, and showing a syringe having a self-sealing male Luer connector at its distal end for connection to the female Luer connector port, a distal end male Luer connector on the tubing, a roller clamp to control the rate of flow of medical fluid through the IV medical fluid administration set ("IV set"), and a waste-bin for use in priming the IV administration system.

Referring now to the drawings in more detail in which like reference numerals refer to like or corresponding elements among the views, there is shown in FIG. 1 a view of an IV administration system 20 having a container 22 of medical fluid for administration to a patient, a drip chamber 24, tubing 26, three Y-sites 28, 30, and 32, a roller clamp 34, and a connector 38 located at the distal end 36. A waste-bin 40 is shown for use in priming the IV system. Also shown is a syringe 42 for use in injecting fluid into one of the Y-sites; in this case, the most distal Y-site 32. The syringe may also be used to withdraw fluid from the IV set. The FIG. also shows leakage 44 of fluid from the distal end of the IV set into the waste-bin during the priming process.

As described above in the background section, a clinician would typically hold the distal end connector 38 in one hand and manipulate the roller clamp 34 with the other hand to prime the IV set 20. The clinician watches the distal end connector for the flow of liquid to know when the set has been purged of air. Unfortunately, some leakage 44 may occur into the waste-bin 40. If the medical liquid in the set is expensive or toxic, leakage is undesirable, as previously described in detail. Having some type priming device located at the distal end connector that accomplishes priming but does not permit leakage would be desirable.

Figures 2, 3:
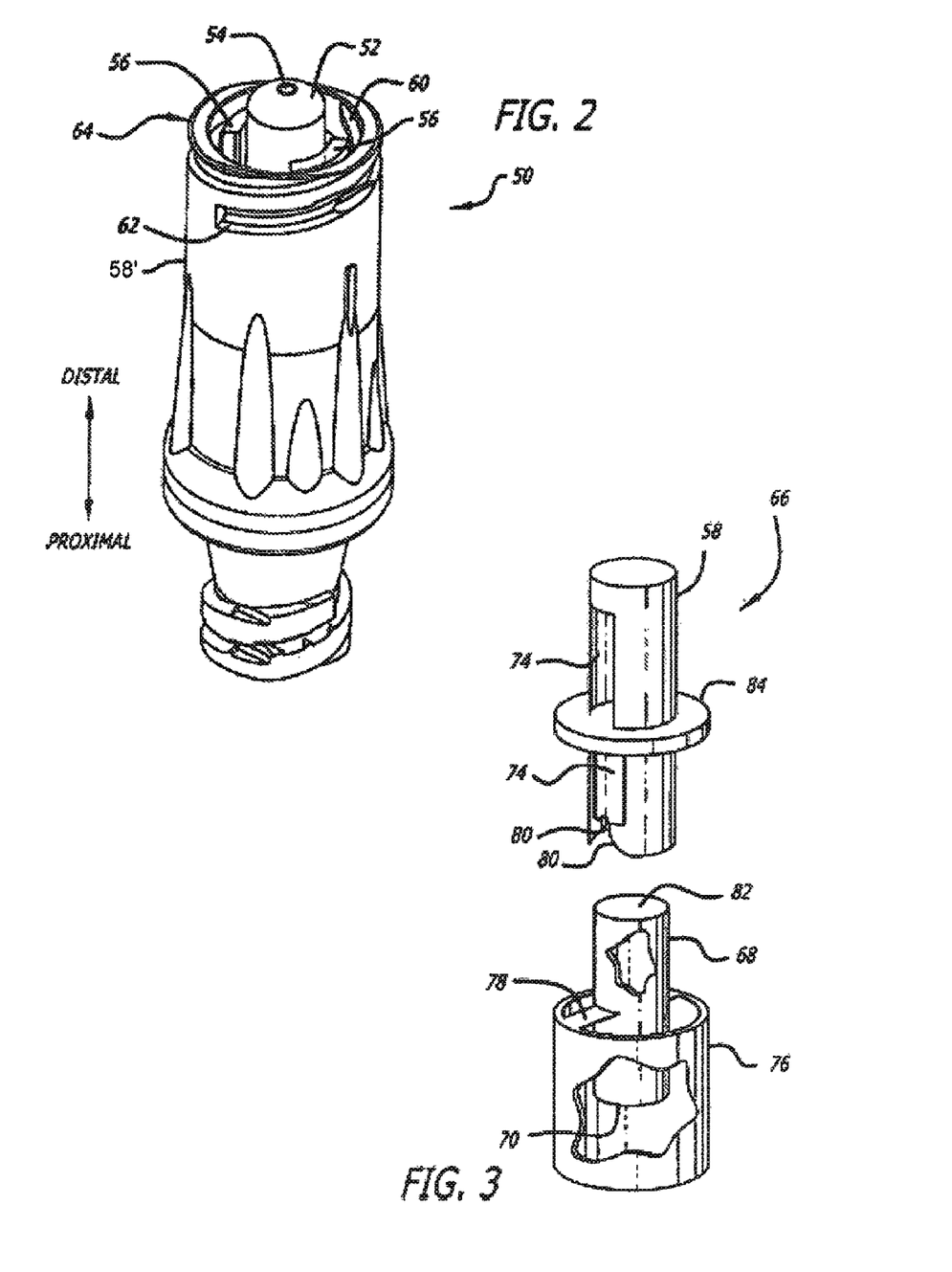
FIG. 2 provides an illustration of a self-sealing male Luer connector having an internal valve with activation arms located adjacent the male connection tip, the internal valve of the shown male Luer connector configured so as to draw fluid back into the connection tip of the connector during de-activation of the internal valve to the non-flow configuration.
FIG. 3 illustrates an exploded perspective view of a protective priming cap in accordance with aspects of the invention showing a reservoir device with a threaded collar partially broken away so that the first opening of the reservoir device may be seen, further showing a window in the outer slidable housing device for viewing the level of liquid in the internal reservoir, and further showing retaining ears on the housing device that retain the reservoir device and housing device connected once assembled.

FIG. 2 presents a perspective view of a self-sealing male Luer connector 50 having a male Luer connection tip 52 with a fluid flow aperture 54 and activation arms 56 forming a part of an internal valve and used to activate the internal valve to a flow configuration and to de-activate the internal valve to a non-flow configuration. The male Luer connector also includes an outer housing device 58' with internal threads 60 surrounding the male connection tip. This particular male Luer connector includes an internal design that draws back a quantity of fluid residing on the connection tip 52 into the connector during the time that the internal valve is being de-activated to the non-flow configuration. This is a safety feature designed into the connector so that any toxic or other fluid left on the connection tip of the male Luer connector will not inadvertently come into contact with a patient or clinician after use of the male connector. The male Luer connector of FIG. 2 also includes external threads 62 at its distal end 64 for engagement with a priming cap, as will be discussed in more detail below.

A protective priming cap 66 incorporating aspects of the invention is shown in an exploded perspective view in FIG. 3. The cap includes an internal reservoir device 68 having a first opening 70 for engaging the aperture 54 of the male connection tip, and a movable outer housing device 58. The outer housing device in this embodiment includes a window 74 through which the reservoir device may be observed. In this embodiment, the reservoir device is formed of a translucent or transparent material, or other clear material that is clear enough to permit visual inspection of the contents of the reservoir device. Through the window in the outer housing device and the through the clear reservoir device, the clinician can view the contents of the reservoir device to determine if gas has been expelled from the reservoir and that the reservoir is now completely full of liquid. In one embodiment, the material used for the reservoir device was polypropylene.

The reservoir device 68 in this embodiment includes an internally threaded collar 76 for engaging the external threads 62 (FIG. 2) of the male Luer device 50. The reservoir device includes two bridges 78 to the threaded collar (one of which can be clearly seen) so that as the threaded collar is rotated to engage the male Luer device threads, the reservoir device will also rotate. The width of the bridges is selected to accept two sets of opposing ramp-shaped retaining ears 80 (one set is shown in FIG. 3) forming a part of the outer housing device 58 in this embodiment. The retaining ears have the ramps to assist in assembling the outer housing device to the reservoir device; i.e., sliding them over the bridges, but the hook-shape of the ramps will retain the two devices in the assembled configuration since disassembly would be difficult. The width of the bridges is selected to be wider than the space between the retaining ears but not to so wide that the opposing ears cannot be slid over the bridges. It will be noted from following figures that the priming cap is assembled by sliding the distal end 82 of the reservoir device into the outer housing device 58 so that the retaining ears slide over the bridges, and then snap back towards each other to their closer positions. The outer housing device also includes a circular external flange 84 located at about one-half way between its proximal and distal ends. The flange assists in stabilizing the movement of the outer housing in activating the internal valve of the male Luer device to the flow configuration, as will be described below.

Figure 4:
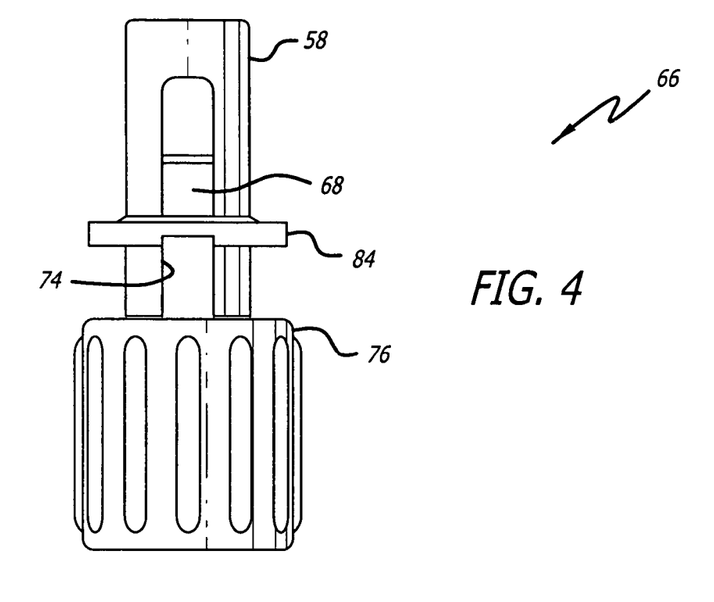
FIG. 4 is a side view of the protective priming cap of FIG. 3 when assembled.

FIG. 4 presents a side view of the priming cap 66 of FIG. 3 in an assembled configuration. The outer housing device 58 is shown over the reservoir device 68 and the reservoir device can be seen through the window 74 of the outer housing device. The flange 84 of the outer housing device is located above the threaded collar 76 of the reservoir device in this view.

Figure 5:
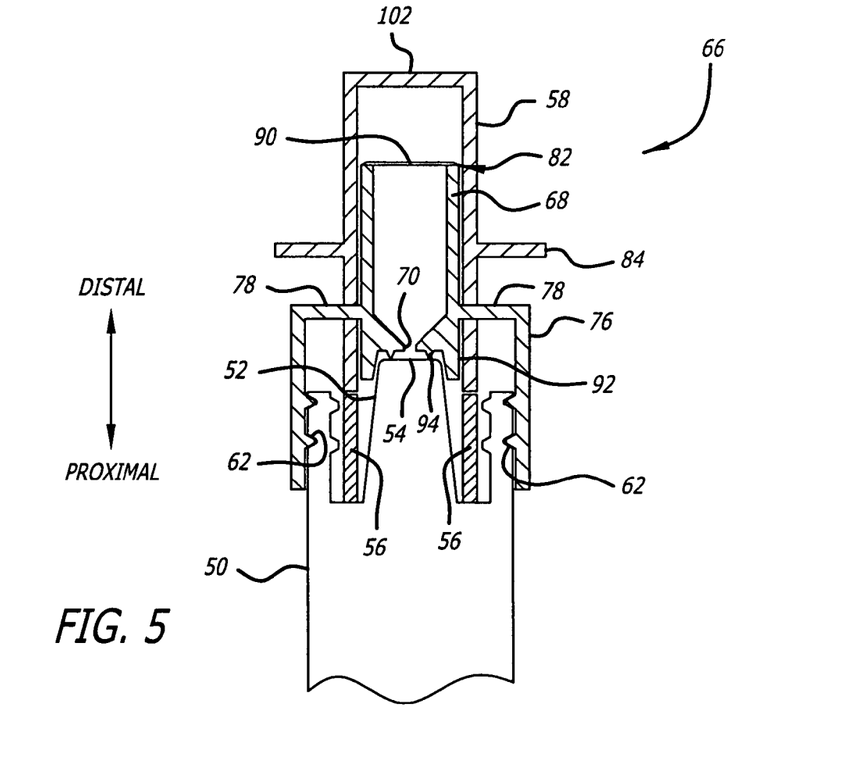
FIG. 5 presents a cross-sectional view of the protective priming cap of FIGS. 3 and 4 in accordance with aspects of the invention mounted to the male self-sealing Luer connector of FIG. 2 so that the male connection tip is protected by the priming cap but the internal valve of the male Luer connector has not been activated to the flow configuration.

Turning now to FIG. 5, a cross-section view of the protective priming cap 66 of FIGS. 3 and 4 is shown assembled with a male Luer connector 50. The priming cap has been mounted to the male Luer connector but the connector is in the non-flow configuration in this figure. The reservoir device 68 includes an hydrophobic membrane or filter 90 at its distal end 82 that is designed to permit gas, such as air, to pass from within the reservoir to the atmosphere while preventing the passage of liquids thereby retaining them within the reservoir. Hydrophobic filters or membranes are commercially available. One example is produced by Millipore, 80 Ashby Road, Bedford, Mass. 01730. The proximal end 92 of the reservoir device 68 is in firm contact with the connection tip 52 of the male Luer connector 50 and is centered on the connection tip so that the aperture 54 of the male Luer connection tip is in fluid connection with the first opening 70 of the reservoir device. Fluids may now flow between the male Luer connector and the reservoir device. Of the fluids that flow into the reservoir device from the male Luer connector, gases will pass out to the atmosphere through the hydrophobic filter but liquid will be retained within the reservoir device. When a clinician notes that only liquid remains in the reservoir device, priming is completed.

Figures 6, 7:
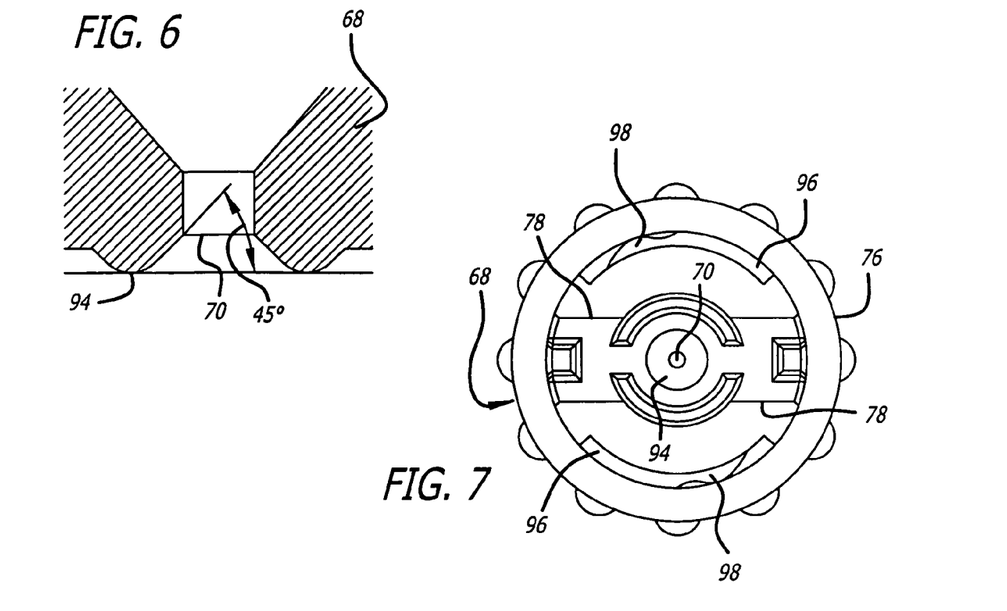
FIG. 6 presents a cross-sectional view of the half O-ring seal at the first opening of the reservoir device embodiment shown herein.
FIG. 7 presents a bottom view of the reservoir device showing a thread design that includes tactile feedback that the clinician has sufficiently tightened the threaded collar to the male Luer connector to establish a suitable seal between the reservoir device and the connection tip of the male Luer connector to avoid leakage of fluids.

Further, the first opening of the reservoir device 68 in this embodiment includes a seal 94. In this case, as shown in FIG. 6, the seal comprises one half of an O-ring. By using a material that is relatively soft and resilient for the reservoir device, such as polypropylene, the seal will provide a sufficient sealing effect with the male Luer connection tip so that leakage will not occur. With this configuration, the seal may be formed as an integral part of the reservoir device. However other types of seals may be devised and used.

Returning to FIG. 5, it will be noted that the threaded collar 76 has been threaded onto the exterior threads 62 of the male Luer connector 50. This threaded connection forces the first opening 70 the reservoir device 68 into intimate contact with the male Luer connection tip 52 so that enough pressure will be placed against the O-ring seal 94 of the reservoir device against the connection tip to avoid leakage. In one embodiment, the clinician simply rotates the threaded collar until sufficient force is developed between the O-ring seal and the connection tip to avoid leakage. In another embodiment, a special thread design is used to provide a tactile feedback to the clinician that sufficient rotation has occurred to develop the necessary force to avoid leakage. Referring now to FIG. 7, a bottom view of the reservoir device 68 is shown. The first opening 70 and O-ring seal 94 can be seen, along with internal threads 96 of the threaded collar 76. A special detent feature 98 is formed in the collar to result in a tactile click when the threaded collar has been rotated a sufficient amount to develop enough sealing force between the O-ring and the connector tip.

Figure 8:
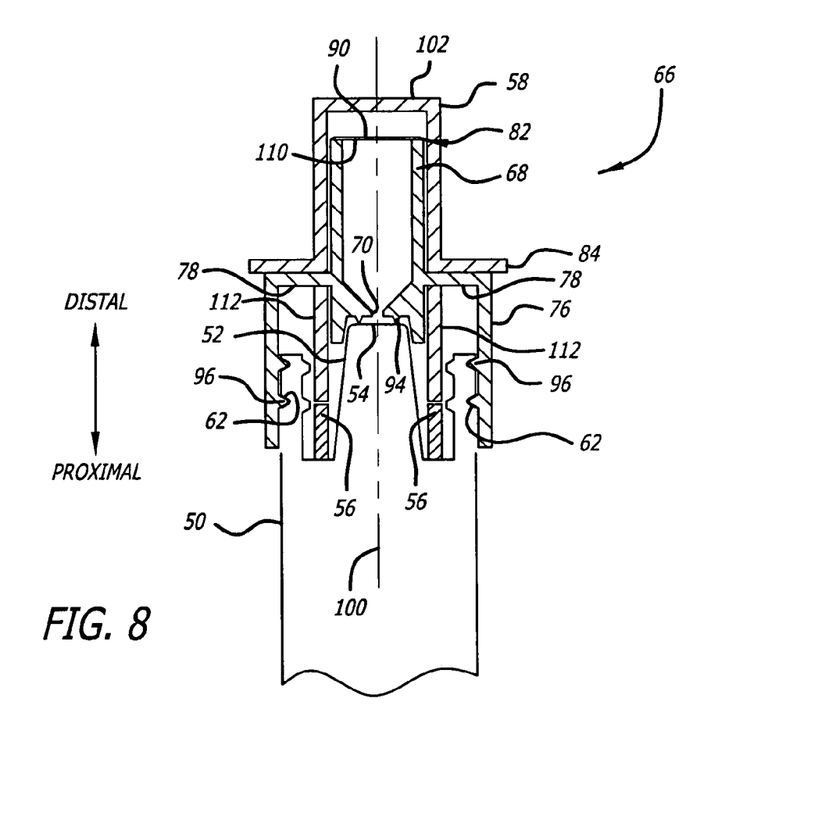
FIG. 8 is a cross-sectional view of the protective priming cap of FIGS. 3 and 4 in accordance with aspects of the invention mounted to the male self-sealing Luer connector of FIG. 2 so that the male connection tip is protected by the priming cap, with the internal valve of the male Luer connector activated by movement of the outer housing device in the proximal direction so that fluid may flow between the reservoir device and the male Luer connector to perform a priming function.

FIG. 8 presents a cross-sectional diagram similar to FIG. 5 in which the outer housing 58 of the priming cap 66 has been slid along the reservoir device 68 in the proximal direction to push the activating arms 56 of the male Luer connector 50 also in the proximal direction to place the internal valve of the male Luer connector in the flow configuration. The flange 84 functions to keep the outer housing oriented along a longitudinal axis 100 priming cap as it is moving in the proximal direction. Significant motion of the outer housing in a direction other than parallel to the longitudinal axis, such as what may be caused by the application of angular force to the distal end 102 of the outer housing device by a clinician, will be prevented by the flange contacting the distal end of the threaded collar 76.

The biasing force of the internal valve of the male Luer connector to the distal direction provides a constant force against the position of the outer housing shown in FIG. 8. Therefore, releasing force on the distal surface 102 of the outer housing will result in its movement back to the configuration shown in FIG. 5. However in a different embodiment not shown here, the priming cap may contain a lock feature that locks the outer housing in the position shown in FIG. 8 so that one-handed priming of an IV administration set or device may be conducted. That is, the clinician would not need to hold both the IV administration set roller clamp or other device while pressing the outer housing in the proximal direction. Instead, the clinician simply presses the outer housing in the proximal direction, locks it at the configuration shown in FIG. 8, which also places the internal valve of the male Luer connector in the flow configuration, and then need only manipulate the roller clamp or other device on the IV set.

In the configuration shown in FIG. 8, the reservoir device 68 can be clearly seen through the window 74 (see FIG. 4) of the outer housing 58. As discussed above, the material of the reservoir device is selected so that the viewer can clearly distinguish air from liquid disposed within the reservoir device, such as polypropylene. The outer housing device in one embodiment is made of a rigid plastic such as acetal. Windows 74 may take different shapes and sizes. The open window formed in the outer housing device in the embodiment shown permits gases escaping from the hydrophobic filter 90 of the reservoir device to be vented to the atmosphere. Additionally, the outer housing device may in another embodiment be formed of a transparent material so that the internal reservoir device can be seen through it.

The flange 84 of the outer housing device 58 may take different shapes other than that shown in the drawings. Because of its general shape and use, the outer housing device may be thought of as a push button. That is, the outer housing device is pushed in the proximal direction, as a button would be, to activate the internal valve of the male Luer connector.

It should also be noted from a study of FIG. 5 that the protective priming cap 66 completely covers the male connection tip 52 (see FIG. 2) of the male Luer connector 50. Thus the priming cap 66 provides mechanical protection of the connection tip while the cap is properly in place. This can be seen in greater detail in the cross-section figures. The protective priming cap also can preserve sterility. Therefore, the connectors may be shipped from the manufacturing facility where they are sterilized with the protective priming cap mounted securely thereto. The cap will then preserve sterility during shipment, initial handling, and priming of the connector as well as provide mechanical protection to the male connection tip.

Referring again to FIG. 8, the reservoir device 68 is in contact with the male connection tip 52 so that the aperture 54 of the connection tip is aligned with the first, or proximal, opening 70 of the reservoir device. Fluid communication between the reservoir device and the male Luer connector 50 is thus possible. Such fluid communication can occur in both the distal and the proximal directions. That is, fluid from the male Luer connector can flow into the reservoir device and fluid from the reservoir device can flow into the male Luer connector. The hydrophobic filter 90 can be seen mounted in place over the second, or distal, opening 110 of the reservoir. The male Luer connector includes an internal valve (not shown) having the activation arms 56 also shown in FIG. 8. It will be noted that the outer housing device 58 includes an engagement portion 112 that contacts the activation arms. Movement of the activation arms in the proximal direction will cause the internal valve of the male Luer connector to move in the proximal direction thus opening the flow aperture 54 of the male Luer connector for fluid transfer. The activation arms are therefore part of the internal valve of the male Luer connector. In the view of FIG. 5, the internal valve of the male Luer connector is in the de-activated, or non-flow, configuration so that the flow aperture of the male Luer connector is closed and fluid cannot enter or leave the male Luer connector. In the view of FIG. 8, the internal valve of the male Luer connector is in the activated, or flow, configuration so that the flow aperture of the male Luer connector is open and fluid can enter or leave the male Luer connector.

With further reference to FIG. 8, the internal valve of the male Luer connector 50 has been placed in the activated configuration thus opening the aperture 54 of the male Luer connector for fluid flow. To achieve this configuration, the outer housing device 58 was pushed in the proximal direction by the clinician so that the housing device engagement portion 112 has pushed the activation arms 56 of the internal valve in the proximal direction thus opening the flow aperture 54 of the male Luer connector. This places the internal valve of the male Luer connector in the flow configuration and permits fluid to flow both out of the male Luer connector into the reservoir device 68 and out of the reservoir device into the male Luer connector. This has caused the outer housing device of the protective priming cap 66 to move farther down the male connection tip 52 so that the cap is more in connection with the male Luer connector. Although not possible to see in this figure, the window 74 of the outer housing device is now more aligned with the reservoir device and the size of the window has been selected so that a substantial portion, if not all, of the reservoir area of the reservoir device can be viewed. This permits the clinician to determine if the reservoir is free of air and contains only liquid, indicating that priming has been completed.

Typically once the protective priming cap 66 has been moved in relation to the male Luer connector 50 to the configuration shown in FIG. 8, the roller clamp 34 of FIG. 1 is opened by the clinician to allow the fluid from the container 22 to pressurize the IV system 20. In the case where the male Luer connector 50 is part of that IV system, fluid from the container under pressure will enter the male Luer connector 50 and because it is in the flow configuration, will then flow into the reservoir device 68. The clinician views the reservoir device for the existence of any air. The hydrophobic filter 90 will permit gases, including air, to vent to the atmosphere leaving only liquid in the reservoir device. Once the clinician sees that only liquid remains in the reservoir device, the male Luer connector is considered to be primed and ready for use. The clinician then releases the outer housing device 58 allowing it to return to the configuration shown in FIG. 5. As the engagement portion 112 of the outer housing device moves distally, the internal valve of the male Luer connector will move toward, the de-activated configuration. In this case, the male Luer connector is designed to automatically draw back fluid through its aperture 54 that may remain on the external surfaces of the connection tip 52 during the de-activation process. Therefore, at the time that the outer housing device reaches the configuration shown in FIG. 5, the male Luer connector has drawn back into itself fluid from the reservoir device, since they remained in fluid communication during the time that the outer housing returned to the FIG. 5 configuration. Because only liquid remains in the reservoir area, the male Luer connector will draw back only liquid and will therefore remain primed. The clinician then grasps the threaded collar 76, rotates the collar to disengage the collar threads 96 from the male Luer connector threads 62, pulls the priming cap from the male Luer connector and discards it.

In the embodiments shown in the various figures, the internal volume of the reservoir device 68 is selected to approximately equal the draw back volume of the internal valve of the male Luer connector. Thus, when the male Luer connector 50 has reached its non-flow configuration as shown in FIG. 5, the male Luer connector will remain primed and the reservoir device will have substantially no liquid remaining within it. The protective priming cap 66 may then be discarded without any loss of expensive medical fluids or the possibility of inadvertent contact of toxic medical fluid with the clinician or patient.

In other embodiments, the reservoir is designed to hold a small amount of liquid in excess of that drawn back into the male Luer connector. However, the first opening 70 of the reservoir device has such a small diameter that it would be difficult to shake the remaining fluid out of the reservoir device after it has been disconnected from the male Luer connector. In another embodiment, ribs or fins or other surface irregularities (such as a shape similar to the teeth of a gear) may be added to the inside surface of the reservoir to increase surface tension of any remaining liquid thereby further inhibiting its escape through the first opening of the reservoir device after disconnection of the priming cap from the male Luer connector.

Prior to assembly to the male Luer connector 50, the reservoir device 68 with its hydrophobic filter or membrane 90 is snapped into the outer housing device 58. The outer housing device is free to slide distally and proximally in relation to the reservoir device, but the retaining ears 80 of the outer housing device prevents the outer housing device from moving so far distally that it falls free of the reservoir device. Prior to priming, the protective priming cap 66 must be attached to the male Luer connector 50 as shown in FIGS. 5 and 8. The threaded collar 76 is placed in contact with the connection end of the male Luer connector and the collar rotated to engage the threads and pull the first opening 70 of the reservoir device into contact with the connection tip 52 of the male Luer connector. The threaded collar is rotated until the tactile click is felt indicating that the priming cap is in position on the male Luer connector for priming. Fluid communication between the reservoir and the male Luer connector may then be established by moving the outer housing in the proximal direction. While a spring is not shown in the priming cap embodiment in the figures, the internal valve of the male Luer connector includes a spring that tends to return the valve to the de-activated configuration and the male Luer connector to the non-flow configuration and consequently, tends to cause the outer housing to return to the distal position shown in FIG. 5.

If the clinician were using a syringe directly connected to the male Luer connector 50 to prime the male Luer connector, he/she will not only see the liquid contact the hydrophobic membrane 90, but he/she will also feel a sudden change in pressure against the syringe plunger at this point. Due to its hydrophobic nature, the membrane will not allow liquid to pass. When the clinician sees the liquid contact the membrane, he/she either stops pressurizing the male Luer connector or releases the outer housing device 58 to stop flow (or both). Because the internal valve of the male Luer connector is spring-loaded, it will push the outer housing device in the distal direction once it is released until the fluid pathway through the male Luer connector is closed again.

The invention thus provides a very efficient, lower cost means to prevent medical fluid from spilling, and maintains a closed system even while priming. The protective priming cap provides protection of the male connection tip as well as providing a means to maintain the primed configuration of the male Luer connector even when being removed from it.

The terms "proximal" and "distal" directions are provided, referenced, and indicated in this detailed description and in the drawings for reference only. They provide only relative directions of movement or of position for ease in description and illustration and are not meant to be limiting of the invention.

Although the present invention has been described in terms of certain preferred embodiments, other embodiments that are apparent to those of ordinary skill in the art are also within the scope of the invention. Accordingly, the scope of the invention is intended to be defined only by reference to the appended claims. While variations have been described and shown, it is to be understood that these variations are merely exemplary of the present invention and are by no means meant to be limiting.

We claim:

1. A cap for a medical connector, the connector having a distal end at which is disposed a distal connection tip, the connection tip having an aperture through which fluid may flow, and the connector having an internal valve, the cap comprising:
    a reservoir device having an internal volume, a first opening at a proximal end, and a second opening;
    an hydrophobic filter disposed over the second opening of the reservoir device;
    wherein the proximal end of the reservoir device is shaped for engaging the connection tip of the connector so that the first opening of the reservoir device may be put into fluid communication with the aperture of the connector, the reservoir device being removable from the connector; and
    an outer housing device mounted over the reservoir device and movable in relation thereto, the outer housing device covering the distal connection tip of the connector whereby it provides protection to the distal connection tip, the housing device including an engagement portion disposed to engage the internal valve of the connector;
    wherein the outer housing device is movable to a first position at which it covers the distal connection tip of the connector but the engagement portion does not open the internal valve of the connector and is movable to a second position at which the outer housing device covers the distal connection tip of the connector and the engagement portion opens the internal valve of the connector so that fluid flow may occur between the reservoir device and the connector, the outer housing device being removable from the connector.

2. The cap of claim 1 wherein the reservoir device is formed of a transparent material so that a level of liquid within the reservoir device may be seen.

3. The cap of claim 2 wherein the outer housing device includes a window through which the level of liquid in the reservoir device can be seen through the outer housing device.

4. The cap of claim 2 wherein the outer housing device is formed at least partially of a transparent material so that the level of liquid in the reservoir device can be seen through the outer housing device.

5. The cap of claim 1 wherein the distal connection tip comprises a male Luer tip and the reservoir device has a shape complementary to the male Luer tip allowing the reservoir tip to mate with the male Luer tip for communication of fluid between the two.

6. The cap of claim 1 wherein the outer housing device is slidable along the reservoir device between the first and second positions.

7. The cap of claim 1 wherein the reservoir device is attached to the connector.

8. The cap of claim 7 wherein the reservoir device is threaded to the connector to establish attachment.

9. The cap of claim 8 further comprising a tactile structure configured to provide a tactile feedback to a clinician rotating the reservoir device in relation to the connector when the reservoir device has been threadably rotated sufficiently to establish a seal with the connector.

10. The cap of claim 1 wherein the reservoir device comprises an inner surface having irregularities configured to, increase the surface tension of liquid within the reservoir whereby escape of the liquid from the reservoir device is inhibited.

11. The cap of claim 1 wherein the reservoir device is assembled within the outer housing device to form the cap and is removed from the connector as one piece.

12. The cap of claim 1 further comprising a lock device configured to retain the outer housing device in a position at which an internal valve of the connector is activated to a flow position.

13. A method for priming a medical connector, the connector having a distal end at which is disposed a distal connection tip, the connection tip having an aperture through which fluid may flow, and the connector having an internal valve, the method comprising:
    mounting a reservoir device having an internal volume, a first opening at a proximal end, and a second opening at which is disposed an hydrophobic filter at the connection tip of the connector with the first opening in fluid communication with the aperture of the connection tip;
    activating the internal valve of the connector to a flow configuration while covering the connection tip;
    allowing fluid to flow through the connector and into the reservoir;
    de-activating the internal valve of the connector to a non-flow configuration while covering the connection tip; and
    removing the reservoir device from the connection tip.

14. The method of claim 13 further comprising moving a housing device mounted over the reservoir device to activate and de-activate the internal valve of the connector.

15. The method of claim 13 further comprising observing the flow of fluid into the reservoir through the reservoir device.

16. The method of claim 15 further comprising:
    moving a housing device mounted over the reservoir device to activate and de-activate the internal valve of the connector; and
    monitoring the flow of fluid into the reservoir through an opening formed in the housing device.

17. The method of claim 13 further comprising storing in the reservoir device a quantity of liquid approximately equal to a quantity of fluid drawn back into the connector when its internal valve is de-activated.

* * * * *